United States Patent
Käs et al.

(10) Patent No.: US 9,683,982 B2
(45) Date of Patent: Jun. 20, 2017

(54) METHOD FOR DIAGNOSIS AND/OR PROGNOSIS OF CANCERS BY ANALYSIS OF THE MECHANICAL PROPERTIES OF TUMOR CELLS

(71) Applicant: Universität Leipzig, Leipzig (DE)

(72) Inventors: Josef Käs, Leipzig (DE); Jochen Guck, Leipzig (DE)

(73) Assignee: Universität Leipzig, Leipzig (DE)

( * ) Notice: Subject to any disclaimer, the term of this patent is extended or adjusted under 35 U.S.C. 154(b) by 0 days.

(21) Appl. No.: 14/678,156

(22) Filed: Apr. 3, 2015

(65) Prior Publication Data

US 2015/0276706 A1    Oct. 1, 2015

Related U.S. Application Data

(63) Continuation-in-part of application No. 13/877,452, filed as application No. PCT/EP2011/067271 on Oct. 4, 2011, now abandoned.

(30) Foreign Application Priority Data

Oct. 4, 2010   (DE) ........................ 10 2010 041 912

(51) Int. Cl.
 *G01N 33/483*  (2006.01)
 *G01N 33/50*   (2006.01)
 *G01L 1/24*    (2006.01)

(52) U.S. Cl.
 CPC ............ *G01N 33/4833* (2013.01); *G01L 1/24* (2013.01); *G01L 1/241* (2013.01); *G01N 33/5011* (2013.01)

(58) Field of Classification Search
 None
 See application file for complete search history.

(56) References Cited

U.S. PATENT DOCUMENTS 6,067,859 A * 5/2000 Kas .................. G21K 1/006
                                                  250/251

OTHER PUBLICATIONS

Guck et al. Optical Deformability as an Inherent Cell Marker for Testing Malignant nTransformation and Metastatic Competence. Biophysical Journal (2005), v88, p. 3689-3698.*
Cross et al. Nanomechanical analysis of cells from cancer patients. Nature Nanotechnology (2007), v2, p. 780-783.*
Remmerbach et al. Oral Cancer Diagnosis by Mechanical Phenotyping. Cancer Res (2009), v69(5), p. 1728-1732.*
Fritsch et al. Are biomechanical changes necessary for tumour progression? Nature Physics (epub Oct. 2, 2010), v6, p. 730-732 and appended epub. date.*
Kim et al. Microengineered Platforms for Cell Mechanobiology. Annu. Rev. Biomed. Eng. (2009), v11, p. 203-33.*
Thouimne et al. Time scale dependent viscoelastic and contractile regimesin fibroblasts probed by microplate manipulation. Journal of Cell Science (1997), v110, p. 2109-2116.*
Mierke et al. Contractile forces in tumor cell migration. European Journal of Cell Biology (2008a), v87, p. 669-676.*
Mierke et al. Breakdown of the Endothelial Barrier Function in Tumor Cell Transmigration. Biophysical Journal (2008b), v94, 2832-2846.*
Qi et al. Aurora-B expression and its correlation with cell proliferation and metastasis in oral cancer. Virchows Arch (2007), v450, p. 297-302.*

* cited by examiner

*Primary Examiner* — Scott Long
*Assistant Examiner* — Sean C Barron
(74) *Attorney, Agent, or Firm* — Gudrun E. Huckett

(57) ABSTRACT

In a method for diagnosing and/or prognosis of cancers, diagnosing origin of tumor cells, optimizing cancer therapy, and screening active substances for oncology, the mechanical properties of tumor cells and reference cells are analyzed under mechanical load that causes linear or non-linear deformation of the loaded cell. The engineering strain of the cells caused by directed mechanical stress being introduced is used to determine metastasis risk and the presence of uncontrollably proliferating and/or invasive cells, or the origin of the tumor. The metastasis risk is determined based on the proportion of cells in the sample exhibiting engineering strain in a direction opposite to the stressing direction. The risk of the presence of uncontrollably proliferating cells for non-linear deformation of the cell is determined in the sample based on the mean value of the engineering strain in the direction of cell stressing.

7 Claims, 6 Drawing Sheets

METHOD FOR DIAGNOSIS AND/OR PROGNOSIS OF CANCERS BY ANALYSIS OF THE MECHANICAL PROPERTIES OF TUMOR CELLS

CROSS-REFERENCE TO RELATED APPLICATIONS

This application is a CONTINUATION-IN-PART application of U.S. application Ser. No. 13/877,452 having a 35 U.S.C. 371 completion date of 4 Jun. 2013, which application is a national stage filing of international application No. PCT/EP2011/067271 having an international filing date of 4 Oct. 2011 and designating the United States, the international application claiming a priority date of 4 Oct. 2010, based on prior filed German patent application No. 10 2010 041 912.5, the entire contents of the aforesaid U.S. application, of the aforesaid international application, and the aforesaid German patent application being incorporated herein by reference.

BACKGROUND OF THE INVENTION

The invention relates to a method for diagnosis and/or prognosis of cancers, for diagnosis of the site of origin of tumor cells, for optimizing cancer therapy for patients and for screening active substances in oncology in which the mechanical properties of tumor cells and reference cells from normal tissue are analyzed and the diagnosis and/or prognosis of cancers is determined from the engineering strain of the cells resulting from the input of a directed mechanical stress. The invention is used in research, medicine and pharmacy.

The term cancer and cancers summarize an entire class of diseases, which have in common that they form malignant tumors. To date, more than 200 different tumors were identified. Characteristic of all malignant tumors is the uncontrolled proliferation of the cells which are able to displace healthy tissues (invasion of adjacent tissues), and can develop metastases in tissues of the entire body (distant metastases). These three processes are characteristic of the progression of cancer, and they are used as criteria for the classification of cancer in the cancer stages I, II, III and IV (or A-D, respectively) or for staging by means of the TNM-classification and thereby for making a statement regarding the aggressiveness of the disease. It can be determined from stage III (C) that the tumor grows beyond its formation region, and displaces the surrounding tissue. From Stage IV (D), distant metastases can be detected. Depending on the stage of cancer, different treatment is recommended in order to achieve successful recovery. In this respect, the assessment of the aggressiveness of tumor cells is of great importance to select the appropriate therapy method for a patient. Further, it is important that a classification can be made as early as possible in order to select an appropriate therapy. Until now, it is not possible, to determine based on primary tumor samples, whether an advanced stage with the formation of metastases is already present. Diagnosis of cancer is confirmed by the patient's symptoms using imaging methods, such as MRT, CT and the like, as well as by the detection of specific tumor markers. Tumor markers are predominantly proteins and peptides, which are detected in the blood or other body fluids of the patient or on the cell surface, their elevated concentration being indicative of a tumor. Since malignant tumor cells develop from mutated cells of normal tissue, the tumor markers are detectable in cells of normal tissue and are in tumors characterized only by their different frequency of occurrence. A plurality of different tumor markers have been associated with various cancers. Due to their low specificity for tumor cells, they are predominantly unsuitable for diagnostic purposes. Classification into cancer stages by means of tumor markers is currently not possible. For a final diagnosis, pathological examination of tumor sections is currently performed. To analyze how far a tumor has progressed, it is with current testing methods necessary to directly search for the tumor metastasis and to remove, for example suspicious tissue (e.g., lymph nodes).

In this manner and by using imaging methods, it is possible to classify the cancer. Metastasis can be determined only at the time when they have formed sufficiently large cell structures, so that they are visible with the respective method. An incipient metastasis, however, is difficult to prove.

Differing from the widespread analysis of proteins, in particular surface proteins, as tumor markers, and thereby from the analysis of biochemical properties of the cell for diagnosis or prognosis of cancer, it has been found that, compared with cells from normal tissue, tumor cells have undergone changes in the cytoskeleton resulting in a change in the mechanical (herein also "biomechanical") properties of the cell.

It is known that based on the mechanical properties of the cytoskeleton of cells, a statement can be made about the proliferation of the cells [Lekka at al. 1999, Guck et al. 2005, Cross et al. 2007, Remmerbach et al. 2009]. It was found that tumor cells, i.e. cells which proliferate uncontrollably, have a higher deformability compared with normal tissue. Further increased deformation was for breast cancer also associated with a risk for the migration of cells and thus the formation of metastases [Guck et al. 2005, Ward et al. 1991]. This higher deformability of the tumor cells was accounted for by the fact that actin filaments of the cells being present in the interphase are regressed with the cell entering into mitosis and actin is thereafter present in diffuse distribution in the cytoplasm of cells [Sanger et al. 1975]. It is further assumed that actin is downregulated in tumor cells [Rao & Cohen 1991]. Especially actin in the form of filaments aids stabilizing the cells, so that higher deformability of the cells can be used as a suitable marker for the uncontrolled proliferation of cells. This increased deformability of the tumor cells is observed under mechanical loads, which result in linear deformation of the cell. Besides actin, other cytoskeleton elements such as microtubules, intermediate filaments and their associated crosslink and motor proteins have influence on cell mechanics.

U.S. Pat. No. 6,067,859 with the so-called optical stretcher discloses a method with which deformation of cells can be caused under a load. In this, deforming mechanical stress is by means of laser beams in opposite direction applied to the cells to be analyzed resulting in viscoelastic deformation of the cell. The tension stress being generated by the laser beams at the time of load application (application of the mechanical stress) results in an elongation of the cell along the major axis of the cell, which is oriented along the laser beams. The engineering strain thus determined, i.e. the relative change in length of the cell along the direction of direction of stressing is greater for tumor cells than for normal tissue. The change in length of the cell is optically monitored by a microscope, so that the engineering strain can be determined.

Alone the statement that cells have higher deformability is not yet sufficient for any diagnosis or prognosis of cancer. Also other cells currently being in the midst of division exhibit such changes of the cytoskeleton. To establish a reliable prognosis of cancer, a statement about the likelihood of metastases or the invasion of the cells into surrounding tissue, respectively, must be made. As already stated, metastasis can currently only be determined at a relatively late stage, namely after the formation of metastases, by means of imaging methods.

There is therefore a need to characterize metastatic or invasive cells by specific properties of the cytoskeleton and use these properties for the diagnosis and/or prognosis of cancers. By means of special biomechanical properties being associated with the likelihood of metastases or invasiveness of cells, there is a new therapeutic approach in cancer therapy, in that the mechanical properties of the cell are changed. There is also a need for thus selecting active substances for the treatment of a patient by patient-specific active substance screening, so as to improve the chances of recovery.

The object of the invention is to provide a method by means of which a statement regarding the risk of tumor metastases and possibly the presence of invasive cells in a patient can be made by analyzing previously unknown mechanical properties of tumor cells. It is a further object of the invention to provide a screening method used to identify the potential active substances for cancer therapy which affect the biomechanical properties of the tumor cells. Another object of the invention is to enable an individualized therapy adapted to the needs of the patient by specific active substance screening. Furthermore, it is an object of the invention to draw conclusions about the site of origin of a tumor by means of analyzing the biomechanical properties of tumor cells of a patient.

SUMMARY OF THE INVENTION

According to the invention, the object is solved by a method for diagnosis and/or prognosis of cancers comprising the analysis of the engineering strain of cells under a mechanical load, where the cells are obtainable from a sample of biological material of a patient (hereinafter referred to as patient's sample). In the method for diagnosis and/or prognosis according to the invention a) deforming mechanical stress is applied as a mechanical load to a respective cell in such a manner that linear deformation of the cell is to be expected. At the time of mechanical load application, the engineering strain of the cell along the direction of stressing, is determined.

b) The proportion of cells in the patient's sample which under a mechanical load exhibit engineering strain in a direction opposite to the direction of stressing is compared with reference data. In this, a proportion of cells, under a mechanical load exhibiting engineering strain being in a direction opposite to the direction of stressing, which is higher than in the reference data, indicates a higher risk of tumor metastases in the patient's sample.

The invention is based on the discovery that in the analysis of tumor cells in an optical stretcher while applying a low mechanical stress of 1-2 Pa, a small proportion of the cells exhibits no positive engineering strain in the direction of stressing, i.e. a positive relative change in length, but on the contrary shows contractile behavior (engineering strain in a direction opposite to the direction of stressing). This means that under the mechanical load, reduction of the cell diameter ("contraction of the cell") has been detected although the mechanical stress applied should actually cause an increase in the cell diameter. This behavior here indicates an engineering strain which is directed opposite to the direction of stressing.

It was found by the inventors that in normal tissue samples there are no or only very few cells having this property, whereas in tissue samples from tumors, a significantly higher proportion of these cells exists. The frequency of occurrence of the cells which under a directed mechanical load exhibits engineering strain in a direction opposite to the direction of stressing was quantified in exemplary tissue samples from tumors at about one cell per 100 cells.

These cells were isolated and exhibited biological properties differing from those of the other cells from the tumor tissue (which in the optical stretcher exhibited positive engineering strain under a mechanical load). These properties indicate that these cells are involved in metastasis. A co-culture of cells from normal tissue with unsorted cells from tumor tissue (T1b classification) showed that the tumor cells during culturing isolate themselves from the normal tissue and form clusters. The tumor cells during growth therefore showed an affinity to cells of the same type and thereby cluster together during culturing. Any mixing with normal tissue barely occurs. Especially during metastasis, however, there is a transition of tumor cells into tissues of other origin. A co-culture of cells from normal tissue with sorted contractile cells from tumor tissue (T3b and T4 classification) showed that the sorted contractile tumor cells form no clusters and mixing is maintained with the cells of normal tissue during culturing. The sorted contractile cells therefore have lost the affinity to cells of similar type (FIG. 2). A higher proportion of cells in the sample under a mechanical load exhibiting engineering strain in a direction opposite to the direction of stressing in comparison with reference data from normal tissues therefore means that the analyzed sample contains more cells that can metastasize.

By analyzing these mechanical properties (contractile behavior under a mechanical load in the linear deformation range) of tumor cells, a statement can thereby be made as to whether an increased risk of tumor metastasis is given.

It is also known that cells of tumor tissue under a mechanical load in a region in which linear deformation of the cell is to be expected, firstly contain a higher proportion of cells having an increased positive engineering strain under tensile load (i.e. engineering strain in the direction of stressing) as compared with cells of normal tissue, and that secondly, the range of engineering strain is larger than for cells of normal tissue. The reason given for this is the dissolution of the actin filaments of the cytoskeleton of the cells after entry into mitosis. This higher strainability of tumor cells under mechanical loads causing linear deformation of the cell can additionally be used as a measure for the presence of uncontrollably proliferating cells. Metastatic cells in comparison to non-metastatic tumor cells have an even higher deformability. Also the range of engineering strain is even higher (FIG. 3). To this end, higher deformability of the cells of the patient's sample as compared with cells of normal tissue can be used both for determining an increased risk of the presence of uncontrollably proliferating cells as well as for determining the risk of metastasis. As in the analysis of the engineering strain of cells of a patient's sample under a mechanical load, the comparison is usually performed with only one reference sample, any substantiated statement on the metastasis risk additionally requires considering the proportion of cells that exhibit an engineering strain in a direction opposite to the direction of stressing under mechanical load. The finding alone, that a higher proportion of cells is given in the patient's sample, which exhibit an engineering strain under a mechanical load that is higher than that of the cells of the normal tissue, is not sufficient to make a reliable statement about the risk of metastasis because a reference is required for this and no absolute limit values are sufficient for such determination. For this, further comparison with non-metastatic tumor cells would be necessary, which, however, are usually not available from the same patient. To this end, the finding, that a higher proportion of cells given in the patient's sample, which under a mechanical load exhibit an engineering strain in a direction opposite to the direction of stressing, in combination with the finding that the range of engineering strain of the cells in the direction of stressing and the mean value of this stress in the patient's sample is significantly higher than in the reference sample (e.g., normal tissue) is very beneficial for detecting an increased risk of metastasis. But it is already possible to determine the risk of tumor metastasis alone from the higher proportion of cells having an engineering strain in a direction opposite to the direction of stressing in the sample in comparison to the reference sample.

The method according to the invention additionally preferably comprises determining whether a risk of uncontrollably proliferating cells is given in the sample, where c) the mean value of the engineering strain of the analyzed cells in the patient's sample, which under mechanical load exhibit engineering strain in a direction opposite to the direction of stressing is compared with reference data. In this, a mean value of the engineering strain in the direction of stressing in the patient's sample being higher than in the reference data indicates a higher risk of the presence of uncontrollably proliferating cells.

If during mechanical loads in a region in which linear deformation of the cell is to be expected, there is both a higher proportion of cells under stress exhibiting engineering strain in a direction opposite to the direction of stressing, as well as a higher mean value of engineering strain in the direction of stressing, each in comparison to the reference data, then the patient is at a high risk of having an aggressive tumor as is caused by uncontrolled proliferation and by the presence of tumor cells which can form metastasis.

In addition to the mean value of the engineering strain of the cells (exhibiting an engineering strain in the direction of stressing), preferably additionally the distribution (frequency of distribution) of the engineering strain of cells exhibiting an engineering strain in the direction of the deforming stress is considered. Not only a higher mean value, but also differences in the distribution of the engineering strain can be used for a statement regarding the risk of the presence of uncontrollably proliferating cells.

For comparison of the distribution, preferably the mean value and the standard deviation (in a normal distribution of the sample) or, respectively, the median and the distance between 25% and 75% quantile (for non-normal distribution) as well as possibly the minimum and maximum engineering strain in the direction of stressing of the examined cells of the sample are compared. If a method according to the invention is performed according to the principle of the optical stretcher, then both a higher mean value and a higher standard deviation (for a normal distribution of the sample), or, respectively, a higher median and greater distance between 25% and 75% quantile (for non-normal distribution), and a smaller minimum and/or a higher maximum engineering strain (in the direction of stressing) are an indication of the presence of uncontrollably proliferating cells.

A distribution is then considered to be closer, if the standard deviation (for normal distribution) or the distance between 25% and 75% quantile (for non-normal distribution) is less in comparison with reference data.

In one embodiment of the invention, in alternative or in addition to the engineering strain of the cell under mechanical load, also the relaxation behavior of the cell is analyzed. As a parameter for the relaxation behavior, the relative relaxation is determined, indicating how far the cell returns to its initial state (before the application of a mechanical load). For determining the relative relaxation, the following parameters are determined:

The original length of the cell prior to the measurement, without applying any mechanical stress ($L_0$);

then the length of the cell during application of a mechanical stress, at which linear deformation of the cell is expected ($L_S$), where the length $L_S$ is determined at a time $t_S$ at which the mechanical stress is still being applied to the cell;

then the length of the cell in the absence of mechanical stress ($L_R$), where the length $L_R$ is determined at a time $t_R$ at which the mechanical stress is no longer applied to the cell (preferably $t_R$ is between 1 and 5 seconds after the mechanical stress is no longer applied to the cell).

After no mechanical stress is any longer applied to the cell, it relaxes in the direction of its original state. The relative relaxation of the cell is determined from the difference of the engineering strain (relative deformation of the cell) after relaxation of the cell at the time $t_R$ and the engineering strain under the application of stress at the time $t_S$. Accordingly, the relative relaxation R of the cell can be described by the following relationship:

$$R=(L_R-L_S)/L_0 \qquad (1)$$

By determining the relaxation behavior, a statement about the risk of the presence of uncontrollably proliferating cells and about the presence of invasive cells can advantageously be made. It is furthermore true: the smaller the mean value of the relative relaxation R of the cells of the patient's sample, the higher the risk of tumor metastases.

Determining the relaxation behavior is based on the following observation:

It is assumed that cells are viscoelastic objects which can actively change their cell shape. With purely elastic objects, deformation and relaxation are mirrored processes, whereas in purely viscous objects there is absolutely no relaxation. When examining a viscoelastic object such as a cell, it is expected that cells which are stiffer (which when introducing a mechanical stress exhibit less engineering strain) also relax more. Conversely, for tumor cells, which exhibit greater engineering strain than cells from normal tissue (for which linear deformation of the cell is to be expected when introducing mechanical stress), weaker relaxation is expected than in cells from normal tissue. Surprisingly it was shown by means of the analysis of tissue from breast tumors, that tumor cells exhibit the exact opposite behavior, and relax even more than the cells of the normal tissue, in this case breast tissue (FIG. 6). It has been shown that tumor cells relax faster than cells of normal tissue, i.e. their distribution function shows more negative values, and this effect increases with the progression of cancer (tumor staging).

The observation that metastatic cells have an engineering strain behavior in a direction opposite to the direction of stressing (where this is therefore an active deformation behavior of metastatic cells under the introduction of stress). This is confirmed by the observations during the relaxation behavior of the tumor cells. It could be shown that during progression of a cancer, there was an increasing number of cells exhibiting such active deformation behavior. While this property of the cells is only detectable by determining the engineering strain under the introduction of stress when the cells are already such that they can leave the cell structures and form metastases (tumors from stage 3), the active deformation behavior of the cells on the basis of relaxation can already be observed with not-metastasizing cells (stages 1 and 2). This can be explained by the different force necessary for the cell for the respective deformation. For relaxation, the cell must counteract no additionally introduced stress, as is the case for determining the engineering strain when introducing stress. Therefore the cell requires less force for the deformation process of the relaxation than for the deformation under stress. With progression of the disease, the number of cells exhibiting active deformation behavior increases, so that the mean value of the relative relaxation moves ever further towards negative values.

The object according to the invention therefore also comprises a method for diagnosis and/or prognosis of cancers by analyzing the relaxation behavior, comprises the analysis of the engineering strain of cells from a sample of biological material from a patient under a mechanical load and subsequently the engineering strain of the cell in the absence of a mechanical load. The method for diagnosis and/or prognosis is according to the invention performed as follows:

the length $L_0$ of the cell from the patient's sample is determined without applying any mechanical stress, then a mechanical stress, at which linear deformation of the cell is to be expected, is applied to the cell at a time $t_S$ and the length $L_S$ of the cell is determined under the introduction of stress, subsequently, without applying the mechanical stress, the engineering strain of the cell is determined after its relaxation at a time $t_R$.

The relative relaxation R is determined in that the engineering strain $\square(t_S)$ of the cell while introducing stress is determined at a time $t_S$ and the engineering strain $\square(t_R)$ of the cell is determined after relaxation of the cell at the time $t_R$, and the difference between $\square(t_R)$ and $\square(t_S)$ is established.

The engineering strain is defined as above and indicates the relative deformation of the cell. From the length of the cell (L) along the direction of stressing as a function of the time $L(t)=2[r_o+\Delta r(t)]$ (where $r_o$ is the radius of the cell along the direction of stressing in the undeformed state and $\Delta r(t)$ is the additional engineering strain of the cell in relation to the time $t_x$) results the engineering strain $\gamma(t)$ from the relationship $\gamma(t)=\Delta r(t)/r_o$. Preferably the relative relaxation is calculated with formula (1).

The relative relaxation of the cells in the patient's sample is compared with reference data A relative relaxation in the patient's sample in the mean value in comparison being lower than the reference data indicates a higher risk for the presence of uncontrollably proliferating cells. Alternatively thereto or in combination therewith, a smaller number of cells in the patient's sample with a relative relaxation of more than 0 in comparison with the reference data indicates a higher risk of the presence of uncontrollably proliferating cells. Alternatively thereto or in combination therewith, a proportion of at most 1% of the cells of the patient's sample with a relative relaxation of more than 0 indicates a higher risk of the presence of invasive cells.

Preferably, the mean value of the relative relaxation of all cells analyzed as compared with the reference data and a reduced mean value in the patient's sample indicate an increased risk of the presence of uncontrollably proliferating cells. Preferably, the mean value of the relative relaxation of all analyzed cells of the patient's sample of ≤−0,01, preferably −0,05 to −0,01, indicates an increased risk of the presence of uncontrollably proliferating cells.

The method according to the invention for diagnosis and/or prognosis of cancer by analyzing the relaxation behavior of cancer cells after a mechanical load alone is sufficient to make a statement about the risk of the presence of a cancer. Preferably, this method is established in combination with the determination of the proportion of cells which under mechanical loads exhibit engineering strain being in a direction opposite to the direction of stressing (proportion of contractile cells). In this, a proportion of cells, under a mechanical load exhibiting engineering strain in a direction opposite to the direction of stressing, that in the patient's sample is higher than in the reference data and a relative relaxation in the patient's sample on average being lower than in the reference data, indicates a higher risk of tumor metastasis. By means of combining the two methods, more reliable statements regarding the risk of tumor metastases is possible.

Therefore, alone from the analysis of tumor cells under mechanical load, which is introduced by mechanical stress, in the area of linear deformation a statement can be made about the probability of metastasis and the proliferation of the cells as well as the presence of invasive cells.

Further, the inventors have found that tumor cells also under mechanical loads resulting in a non-linear deformation of the cells show characteristic behavior. Compared with cells from normal tissue, tumor cells in the load range of non-linear deformation exhibit higher stiffness than cells of normal tissue when increasing the mechanical load. In this load range (for non-linear deformation), the engineering strain of the tumor cells under load therefore exhibits exactly the opposite tendency as with loads causing linear deformation. The engineering strain of the cell in the direction of stressing under a mechanical load in an area of non-linear deformation is less than the engineering strain of the cells from normal tissue, and the proportion of cells that show little engineering strain under mechanical stress is greater than in normal tissue. It was shown that this higher stiffness of the tumor cells under mechanical loads resulting in non-linear deformation of the cell is characteristic of cells that are invasive. It is believed that the stiffening of the cells under mechanical loads, at which non-linear deformation is to be expected, is caused by microtubules and intermediate filaments.

Tumor cells that invasively spread to surrounding tissues are unlike metastatic cells usually no individual cells leaving the cell structure. Instead, the entire structure of cells spread to the surrounding tissue and thereby displaces the surrounding tissue. This can only occur as long as the resistance caused by the cells of the surrounding tissue is less than the force that is applied by the growth of the tumor Since the tumor cells during high loads have a higher stiffness than non-tumor cells, they can displace or dissolve the cells of the normal tissue which are more expandable under these loads. By means of an illustrative experiment, in which the tumor cells were cultured in a hydrogel with agarose, it was found that tumor cells in the cell structure can withstand stresses of up to 10 kPa (FIG. 5).

It can thereby be derived from the engineering strain under mechanical loads resulting in non-linear deformation of the cell whether an increased risk for the presence of invasive cells is given. In this, the mechanical loads being exerted are significantly higher than those causing linear deformation of the cell.

Therefore, in a method according to the invention, preferably additionally d) at least one cell from the same patient's sample is subjected to a deforming mechanical load applied as a mechanical stress in such a manner that non-linear deformation of the cell is to be expected. The engineering strain of the cell is determined at the time of mechanical load application.

e) The mean value of the engineering strain of the analyzed cells of the patient's sample is compared with reference data. In this, a mean value of the engineering strain in the patient's sample being higher than in the reference sample indicates a higher risk of the presence of invasive cells. These invasive cells allow the tumor to grow against the pressure of the surrounding tissue.

By analyzing the engineering strain of cells from tissue samples under linear and non-linear deformation, a statement on uncontrolled proliferation, invasiveness as well as likelihood of metastasis can therefore be made. In this, it is advantageously possibly by means of the method for diagnosis and/or prognosis to characterize tumor cells by analyzing their mechanical properties and not by analyzing surface markers. This has the advantage that no change in the cell or the like has to be undertaken, for example by staining with antibodies or the like, which can affect its vitality and its functional state. By means of analyzing the mechanical properties of the cells in a method according to the invention for diagnosis and/or prognosis, advantageous classification of the cancer into cancer stages I, II, III and IV or, respectively, into the stages of the TNM classification, is possible. It is even conceivable to perform a more accurate classification than the currently existing classification grid allows, since the risk of the formation of metastasis can be determined already prior to the actual formation of metastases from the cells of the primary tumor (original tumor).

The cells, which are analyzed in a method according to the invention for diagnosis and/or prognosis originate from a sample of biological material from a patient. In this, tissue samples from patients' tumors being removed invasive or minimally invasively are preferred. For minimally invasive removal, punch biopsy, fine-needle biopsy or punctures are preferred. Especially preferred are tissue sample from primary tumors of the patient because it is advantageously possible when analyzing cells from such samples, to determine from the cells of the primary tumor, whether a risk of metastasis is given. For this, preferably cells from a thin section from a surgically removed tumor from the patient are analyzed in a method according to the invention for diagnosis and/or prognosis. However, cells are in a method according to the invention or diagnosis and/or prognosis also preferred which were removed from the patient in non-invasive manner, for example by means of a swab. Cells from swab samples have the advantage that they are already present in individualized form and therefore do not need to be individualized in a complex additional method step. Other preferred cells being analyzed in a method according to the invention for diagnosis and/or prognosis originate from a sample of body fluid from the patient, in particular a blood sample, a sample from a lumbar puncture or a sample from a chest drainage. Of these, cells from a blood sample are most preferable.

Analyzing the engineering strain of cells under load enables cancer diagnosis and/or prognosis. The analyzed mechanical properties are common to a variety of cancers. To this end, the change of these mechanical properties of tumor cells is not characteristic of a particular cancer, but can transferred to the diagnosis and/or prognosis of a plurality of cancers, preferably cancers where solid tumors occur. Preferably, a method according to the invention is used for diagnosis and/or prognosis of breast cancer, cancer of the mouth and pharynx region, lung cancer, cervical cancer, skin cancer, stomach cancer, colon cancer or prostate cancer. Also leukemia cells in comparison to normal white blood cells have a higher proportion of cells that under a mechanical load (linear deformation) exhibit engineering strain in a direction opposite to the direction of stressing.

Preferably, the method according to the invention for diagnosis and/or prognosis of cancer is used in that cells of a tumor tissue sample, in particular a primary tumor sample, from a patient are analyzed and a statement about the likelihood of metastasis and possibly about the invasiveness and/or uncontrolled growth is then made.

Also a classification is in the context of a diagnosis advantageously performed with the method according to the invention from samples of the tumor tissue. Particularly advantageously, in comparison to methods known from prior art, a statement on the formation of metastases can also be made from the primary tumor samples. Diagnosis of cancers and subsequent classification using a method according to the invention is a preferred application.

In addition, for diagnosis purposes, also cells from an individual obtained in non-invasive or minimally invasive manner can be analyzed. This can for example be a smear sample, punch biopsy or fine needle biopsy or a tissue sample of suspicious tissue, e.g. a thin section from a surgically removed tumor. The analysis is preferably performed on vital cells. If there are cells in the sample that proliferate uncontrollably, then the first sign of cancer is given. This is the case where under mechanical load, at which linear deformation is to be expected, a mean value of the engineering strain in the direction of the deforming stress of cells of the individual is given higher that in the reference data and there are possibly differences in the distribution of the engineering strain in the patient's sample compared with the reference data. In the event that the relaxation behavior of the cell is after loading alternatively thereto or in combination therewith determined, then this is further evidence of uncontrollably proliferating cells, if a mean value of relative relaxation of the cells in the patient's sample is lower than compared with the reference data. If in the sample there is also a higher proportion of cells that under a mechanical load exhibit engineering strain in a direction opposite to the direction of stressing (compared with reference data), then an indication of metastasis of a cancer is given.

If the sample under mechanical load, at which non-linear deformation of the cells is to be expected, has a mean value of engineering strain (in the direction of stressing) in the sample from the individual which is lower than in the reference sample, then this is an indication for the presence of invasive cells in cancer. These invasive cells allow the tumor to grow against the pressure of the surrounding tissue.

By combining this data, a statement can be made from a first sample from an individual about whether evidence for cancer is given and if cancer is given, how far it has progressed. For this, it is not absolutely necessary that cells from a tumor tissue sample be analyzed, also cells from samples obtained in a non-invasive or minimally invasive manner can be analyzed, such as blood tests, samples of a puncture or swab samples from patients.

The method according to the invention for diagnosis and/or prognosis always requires comparison of the engineering strain of the analyzed tumor cells or potential tumor cells, respectively, with reference data. This includes data of the analysis of the engineering strain under load of cells of a suitable reference sample, which were analyzed in the same manner as the cells from the patient's sample. For diagnosis and/or prognosis, preferably cells of the same tissue of one or more healthy individuals are used as a reference sample. Alternatively thereto, also cells of healthy tissue from the same patient not being affected by the tumor are equally preferably suitable. For this, in particular after resection of a tumor from a patient, tumor cells and non-tumor cells are individualized and analyzed separately.

According to the principle of the method according to the invention for diagnosis and/or prognosis, it is also possible to draw conclusions on the site of the original tumor by means of analysis of tumor cells in the blood. Tumor cells, in comparison to the original tissue from which they originated, exhibit differences in biomechanical properties. Nevertheless, it is a fact that the tumor cells in the range of their strainability are very similar to the original tissue. Due to the fact that also the cells of the original tissue differ in strainability (for example, cells of the lung tissue are more stainable than cells of the breast tissue), the magnitude of engineering strain (absolute value) determined under a mechanical load can provide a conclusion about the origin of the tumor. For this, tumor cells from a sample of biological material of a patient are analyzed under mechanical stress and the mean value of the engineering strain in the direction of stressing is determined. This mean value is compared with the mean value of the engineering strain (in the direction of stressing) of reference data, for which the engineering strain of cells of different human tissue was determined. The likelihood that the tumor cells originate from a particular original tissue is highest in the data record (tissue) of the reference data in which the absolute difference between the two mean values of engineering strain is least.

For this, the invention also comprises a method for diagnosis of the tissue of origin of tumor cells from a patient, comprising the analysis of the engineering strain of tumor cells under mechanical load, where the tumor cells are obtainable from a sample of biological material from a patient. In the method according to the invention for diagnosis of the tissue of origin of tumor cells a) deforming mechanical stress is applied to a respective tumor cell as a mechanical load such that linear or non-linear deformation of the tumor cell is to be expected. The engineering strain of the tumor cell is determined at the time of mechanical load application.

b) The mean value of engineering strain in the direction of stressing the tumor cells is determined and compared with different sets of reference data, where each set of reference data comprises the mean value of the engineering strain in the direction of stressing the cells of a particular human tissue. That specific tissue of the reference data set is associated as the tissue of origin of the tumor, for which the value of the difference of the mean values of engineering strain between the patient's sample and the reference data set is least.

The cells, which are analyzed in a method according to the invention for diagnosis of the tissue of origin, are obtained from a sample of biological material from a patient and isolated and individualized using known methods. Preferably, the sample of the patient is here obtained in a non- or minimally invasive manner and is no tissue sample of the primary tumor. Preferably, the tumor cells are collected from a sample of body fluid from a patient, more preferably from a blood sample, from a sample of a lumbar puncture or a sample from a thoracic drainage. Very particularly preferably, the tissue of origin of circulating tumor cells is determined from a blood sample from a patient by means of this method according to the invention.

The reference data sets, to which the engineering strain of the circulating tumor cells is compared, are preferably identical to the reference data of a method according to the invention for diagnosis and/or prognosis Since the site of origin of the tumor cells has to first be determined from the patient sample, a variety of reference data sets are compared with the expansion of the tumor cells from the patient sample determined in the method. In this, a reference data set includes results of this engineering strain analysis of defined human tissue, preferably from human normal tissue. By comparing the engineering strain of the tumor cells to a plurality of reference data sets of different tissues, it is possible to predict the site of origin of the tumor. Alternatively to comparing the engineering strain of the tumor cells from the patient's sample with reference data sets from various normal human tissues, data sets are used as reference data which contains the respective results of the engineering strain analysis of defined human tumor tissue. Ideally a reference data set includes data of at least two reference patients and the values of the engineering strain are averaged across the various patient reference samples.

The mechanical properties of the tumor cells indicating the risk of tumor metastasis and the presence of invasive cells were previously unknown. Therefore substances altering the biomechanical properties of cells represent potential active substances in oncology Substances causing the reduction of the deformability of cells under mechanical loads, for which linear deformation of the cell is to be expected, and substances causing an increase of the deformability of cells under mechanical loads, at which non-linear deformation of the cell is expected, are potential active substances in oncology. Furthermore, substances reducing the proportion of tumor cells which under a load, where linear deformation of the cell is to be expected, exhibit engineering strain in a direction opposite to the direction of stressing, are also potential active substances in oncology A particularly high potential for being an active substance in oncology is attributed to substances which cause several of these alterations of the biochemical properties of the cell. Basically, it can be concluded that substances, influencing the mechanical properties of tumor cells such that the proliferation or migration of tumor cells is prevented, may be considered as potential active substances in oncology.

Therefore the invention also comprises a method for screening substances as potential active substances for oncology (screening method), in which the influence of the substances on biomechanical properties of tumor cells is examined in that the engineering strain of a plurality of tumor cells under a mechanical load is analyzed. In this, i) at least one tumor cell
is contacted with a substance, and
deforming mechanical stress is applied to the tumor cell as a mechanical load such that the tumor cell is deformed in a linear or non-linear manner. The engineering strain of the tumor cell is determined at the time of load application.

ii) The engineering strain of the tumor cells contacted with the substance is compared with reference data from the analysis of the engineering strain of untreated tumor cells of the same kind. The substance is then classified as a potential active substance for oncology, when under mechanical loads, at which linear deformation of the cells is to be expected, the proportion of tumor cells, which under a mechanical load exhibit engineering strain being in a direction opposite to the direction of stressing, of the tumor cells contacted with the substance is less than compared with untreated tumor cells.

The substance is preferably classified as a potential active substance for oncology,
- if under mechanical loads, at which linear deformation of the cell is to be expected, the mean value of the engineering strain in the direction of the stressing of the tumor cells contacted with the substance is less when compared with untreated tumor cells and/or
- if under mechanical loads, at which non-linear deformation of the cell is to be expected, the mean value of the engineering strain of the tumor cells contacted with the substance is greater when compared with untreated tumor cells.

Substances analyzed in a screening method according to the invention comprise molecules which are of natural or synthetic origin. Preferred substances to be analyzed in a screening method according to the invention are selected from natural molecules, in particular peptides, proteins, nucleic acids, including in particular siRNA, synthetic organic molecules, in particular, monomers, polymers, synthetic inorganic molecules and small molecules.

In a screening method according to the invention, tumor cells are examined which originate either from a tissue sample from a patient or from a cell line. In a screening method according to the invention, tumor cells from cell lines are preferably used due to their availability and ease of culturability.

In this, analysis of the engineering strain of similar cells not contacted with the substance, but which otherwise were handled identically, serves as reference data (herein also "untreated" cells). When using cell lines, analysis of the engineering strain of untreated tumor cells of the respective cell line therefore serves as a reference. This data is compared with the engineering strain of cells of the same cell line which have been contacted with the substance. When using cells from tissue samples, preferably tumor tissue samples, untreated cells from the same tissue sample are analyzed as a reference.

Particularly preferably, the data is also compared with normal reference data. For collecting the data of the normal reference, non-tumor cells of the same type are used for which the engineering strain is determined according to the same principle as for the tumor cells. If the screening method according to the invention is performed using tumor cell lines, cell lines are used as normal reference which contain no tumor cells. If the method according to the invention is performed with tumor cells from tissue samples, then preferably cells of the same tissue are used as normal reference, which are not degenerate to tumor cells, or alternatively, cells from a healthy individual from the same tissue (if, for example, the screening process is performed on breast cancer cells, then either normal non-tumor cells of the breast tissue from the same patient or cells from breast tissue of a healthy individual are used as normal reference). If the mechanical properties of the tumor cells are modified by contacting the substance in the direction of the properties of the normal reference, then this is also an indication that the substance is a potential active substance for oncology.

The screening method according to the invention is like the method for diagnosis and/or prognosis of cancer based on the effect that the engineering strain of cells during linear or non-linear deformation can be used as a criterion for the aggressiveness of tumor cells. In both methods, the engineering strain of the cell is determined under a mechanical load, wherein the load is applied by a deforming mechanical stress onto the cell and the cell is thereby deformed.

In a preferred screening method according to the invention, the tumor cells are applied a mechanical stress in such a manner that linear deformation of the cell is to be expected. In a further preferred screening method according to the invention, stress is applied in such a manner that non-linear deformation of the cell is to be expected. More preferably, both the engineering strain of the tumor cells is determined under a mechanical load, under which linear deformation is to be expected, as well as the engineering strain under a mechanical load, under which non-linear deformation is expected.

In a particular embodiment of a screening method according to the invention, the engineering strain under a mechanical load of the same tumor cell is determined. In this, the engineering strain of the untreated tumor cell is first determined under load application. For this, a method must be used in which the tumor cell remains vital even after determination of the engineering strain. For this, an optical stretcher is preferably suitable. Then, the tumor cell is contacted with the substance and the engineering strain of the tumor cell contacted with the substance is determined. In this embodiment, the influence of the substance on the mechanical properties of the tumor cells can be determined particularly well, since identical cells are analyzed before and after contacting the substance.

According to the principle of the screening method according to the invention, it is also possible to select a suitable active substance for cancer treatment of an individual patient (personalized therapy). For this, tumor cells from a sample of biological material from a patient are contacted with different active substances and the one active substance is selected for therapy, which of all tested active substances has the greatest impact on the biomechanical properties of the patient's cells, and preferably modifies them such that progression of the disease is counteracted. This can be done by preventing the cell division capacity or the ability to migrate, by killing the cells or by reconstituting the biomechanical properties of the cell to the extent that they are similar to non-tumor cells. For this, active substances are preferably suitable which cause reduction of the engineering strain of the cell (under load in the area of linear deformation) such that cell division is no longer possible. Active substances are likewise suitable which selectively kill tumor cells with a higher average engineering strain in the direction of stressing (as compared to similar non-tumor cells), or selectively kill only tumor cells, which exhibit an engineering strain in a direction opposite to the direction of stressing (for loads in the linear area of deformation) or which prevent engineering strain against the direction of stressing and thus inhibit formation of metastases.

For this, the invention also comprises a method for optimizing the therapy of a patient with cancer in which the influence of different active substances on the biomechanical properties of tumor cells from the patient is examined. In this, a plurality of the tumor cells from the patient is analyzed under a mechanical load, wherein
  i) at least two samples with tumor cells from the patient can be provided, each of which:
  are contacted with an active substance and
  then deforming mechanical stress is applied as a mechanical load to each respective tumor cell of a sample, such that the tumor cell is deformed in a linear or non-linear manner and the engineering strain of the tumor cell is determined at the time of load application.

ii) The engineering strain of the tumor cells contacted with the respective substance is compared with reference data from untreated tumor cells from a patient.

That active substance is selected for therapy from the active substances, for which the sample containing the tumor cells after contacting the active substance in comparison to untreated tumor cells a) under a mechanical load, at which linear deformation of the tumor cell is to be expected, has the lowest proportion of tumor cells exhibiting engineering strain in a direction opposite to the direction of stressing and/or b) under a mechanical load, at which linear deformation of the tumor cell is to be expected, has the lowest mean value of engineering strain of the tumor cells in the direction of stressing and/or c) under a mechanical load, at which non-linear deformation of the cell is to be expected, has the highest mean value of engineering strain of the tumor cells.

In such a method according to the invention for selecting a suitable active substance for therapeutic treatment of a cancer patient, preferably various active substances are examined which are approved for the treatment of the respective cancer of the patient. In this, an active substance is selected as a suitable active substance which fulfills at least one of the criteria a) to c), preferably at least two of the criteria a) to c), ideally all three criteria.

Tumor cells from the patient, which are used in a method according to the invention for optimizing therapy can be obtained in the same manner as samples with patient cells which are used in a method according to the invention for diagnosis and/or prognosis. In this, they preferably originate from a tumor tissue sample from the patient that was obtained in an invasive or minimally invasive manner. Preferably cells of the same sample are first analyzed using a method according to the invention for diagnosis and/or prognosis and then used in a method for optimizing therapy. In this manner, the disease can first be classified and specific active substance screening for the particular patient can be performed based on the patient's cells from the same sample.

Preferably tumor cells from the same patient sample, but certainly tumor cells from the same patient are used as reference cells for comparison of whether the examined active substance has an effect on the tumor cells of the patient.

Prior to the analysis of the cells in a method according to the invention, they are preferably provided individualized, so that a mechanical load can respectively be applied to one cell and the engineering strain is determined under load application. The mechanical properties of individual cells are therefore analyzed. In this, a plurality of cells, preferably at least 10, in particular at least 100 cells, are analyzed in a method according to the invention, and the mean value, and possibly the distribution of engineering strain in the direction of stressing, and the proportion of cells exhibiting engineering strain in a direction opposite to the direction of stressing and possibly the proportion of cells exhibiting engineering strain in the direction of stressing are calculated.

In a method according to the invention, engineering strain for linear and non-linear deformation is preferably determined from the same cell, in that the cell at a point in time is applied a mechanical load such that linear deformation of the cell is to be expected and at another point in time a mechanical load is applied such that non-linear deformation of the cell is to be expected. During an analysis in the optical stretcher being performed in one embodiment of the invention, successively increasing or decreasing mechanical stresses are applied, where for each stressing applied, the engineering strain of the examined cell is determined At this point, some of the terms being used herein in connection with determining the mechanical properties of cells should be defined in more detail:

Engineering strain is in mechanics an indication of the relative change in length, i.e. elongation or shortening of a body, in this case the examined cell under load application. Engineering strain is the ratio of change in length under load application to the original length (along the direction of the deforming mechanical stress), i.e. it is the quotient of the change in length and the original length of the cell. Engineering strain is therefore a dimensionless quantity. If the dimension of the cell under a mechanical load increases, then the engineering strain is positive ("positive engineering strain"), if the dimension of the cell decreases under a mechanical load, then the engineering strain has a negative sign ("negative engineering strain"). When the size of the cell increases in the direction of stressing, then the engineering strain in the direction of stressing bears a positive sign (positive engineering strain in the direction of stressing, e.g. during lengthening of the cell under tension stress) When the size of the cell reduces in the direction of stressing (for example, contraction of the cell under tension stress), then the engineering strain in the direction of stressing bears a negative sign and is therefore in a direction opposite to the direction of stressing. This can be referred to both as a negative engineering strain in the direction of stressing, or as a positive engineering strain in a direction opposite to the direction of stressing.

Engineering strain of the cell is in the method according to the invention determined at the time of mechanical load application and in the direction of load application. In this, the cell diameter is under a mechanical load preferably determined in the direction of load application, compared with the cell diameter before load application and the engineering strain is calculated therefrom. In addition to the cell diameter, all other parameters of the cell are suitable for determining the engineering strain which can be used as a measure for a change in size, in particular the cross-sectional area of the cell, eccentricity, the ratio of the large to the small main axis, the Taylor deformation parameters or the second moment and higher moments of the cell shape. The engineering strain is determined for each individual cell at the time of a specific mechanical load application. In this, multiple cells are successively analyzed. Determination of the engineering strain "at the time of load application" is here understood within the context of the invention such that also an engineering strain can be determined after termination of the mechanical load application, since the cell does not relax immediately after termination of load application. It is particularly advantageous, however, to determine the engineering strain at the actual time of load application.

By analyzing a plurality of individual cells, the necessary parameters (proportion, mean value, distribution of the respective engineering strain) are then determined for the sample examined.

In each of the methods according to the invention, as a mechanical load, mechanical stress is applied which causes deformation of the cell (deforming mechanical stress). This term is presently used in analogy to the definition in mechanics and designates the force exerted per unit area upon a body in an imaginary sectional surface, in the present case upon the cell. The mechanical stress applied to the cell causes deformation of the cell, preferably compressive stress, in particular tension stress or compression stress and/or shear stress, in particular transverse stress is applied for this. In the normal situation, deformation of the cell occurs such that it acts in the direction of stressing. If, therefore, tension stress is applied, then the cell expands in the direction of the tension stress (positive engineering strain), however, if compressive stress is applied, then the cell contracts in the direction of compressive stress (negative engineering strain).

Preferably, tension stress is applied in the method according to the invention. If the cell enlarges in size along the stressing (in this case, positive engineering strain of the cell), then the engineering strain acts in the direction of stressing. When the cell is reduced in size (contraction of the cell, in this case negative engineering strain of the cell) then the engineering strain acts in a direction opposite to the direction of stressing.

Some cells of the tumor tissue do not strain in the direction of the mechanical stress applied to the cell, but exhibit engineering strain in a direction opposite to the direction of stressing. In such a behavior, the cells contract with the application of tension stress or expand when compressive stress is applied to the cells. This property is characteristic of tumor cells, which are tissue-penetrating and can form metastases.

The amplitude of deformation of the cell is dependent upon the load applied, i.e. the engineering strain of the cell depends on the mechanical stress applied to the cell. In this, the stress necessary for deformation can vary among different cell types and, depending on the method used for introducing the stress into the cells, across many orders of magnitude from a few Pa to 100,000 Pa.

Cells are complex biological and mechanical objects. Deformation of cells under a mechanical load is not purely elastic, but at least viscoelastic. A cell, therefore, after terminating application of a mechanical load, relaxes only partially or at least requires a very long time for full relaxation (returning to the original state).

In the linear area of deformation, engineering strain is proportional to the stress. The area in which linear deformation of cells is to be expected differs among cells of different origin. The mechanical stress that is suitable for cells of a particular type of tissue for causing deformation of the cell in the linear range can be determined in a simple manner, in that the engineering strain of the cells of the particular tissue type is determined at a variety of mechanical stresses and the linear range is read from a stress-engineering strain diagram.

In the embodiments of the invention, in which the cells can be analyzed in a method according to the invention following the principle of the optical stretcher, linear deformation can be expected at a mechanical stress of preferably more than 5 Pa for cells which are analyzed using the method according to the invention. In a method of the invention, in which the cells are analyzed following the principle of the optical stretcher, mechanical stresses from 1 Pa to 5 Pa, preferably from 1 Pa to 4 Pa, in particular from 2 Pa to 3 Pa are preferably applied as a mechanical load.

At higher mechanical stresses, the engineering strain of the cell is no longer proportional to the stress. In this range, non-linear deformation of the cell is detected in dependency to the applied stress. In this load range, cells are analyzed in a method for diagnosis and/or prognosis according to the invention in order to make a statement about the presence of invasive cells and in the method for screening and optimizing therapy in order to determine a suitable substance or an active substance that influences this behavior. Here as well, which mechanical stress must be applied in order to effect non-linear deformation of the cell depends on the cell type. This range can also be read from the above-described stress-engineering strain-diagram.

Preferably, a mechanical stress from 10 Pa to 50 kPa is in the method according to the invention applied to a cell, in which the cells are analyzed following the principle of the atomic force microscope (AFM). Preferably, mechanical stress in the range of more than 100 Pa to 50 kPa, particularly preferably, between 5 kPa and 50 kPa is applied.

In each of the methods according to the invention, mechanical stress is applied to the cells such that they experience deformation. The mechanical stress is there in one embodiment of the method according to the invention applied to the cells by forces of electromagnetic radiation, which is preferably generated by the impingement of two opposing laser beams onto a single cell. This is preferably performed following the principle of the optical stretcher.

Determination of the engineering strain is preferably performed by optical methods with which a change in size of the cell can be detected. Determining the engineering strain is preferably performed using a microscope, where the cell diameter is determined during and after load application (i.e. prior to and during the application of mechanical stress) along the direction in which deformation occurs, and the engineering strain is calculated. In a particularly preferred method according to the invention, analysis of the mechanical properties of the cell is performed with an optical stretcher. Analysis in the optical stretcher or introduction of mechanical stress caused by electromagnetic radiation, preferably laser radiation (which is not significantly absorbed by the cells) is particularly advantageous because no damage to the cell is caused, and it can be further cultured after determining the engineering strain. The cell can thus after analysis be recovered and be provided almost unchanged for further analysis or culturing. This is not possible in this form with previous methods in which the surface properties of the cell is determined, for example, by staining with antibodies, since it is not certain to what extent bound antibodies can influence the reactions of the cells.

In further preferred methods according to the invention, the method is determined using atomic force microscopy, dielectrophoretic forces, in particular by using dielectrophoretic cages, microfluidic flows, micro pipettes, optical tweezers, laser diode bars or ultrasound microscopy, where atomic force microscopy is particularly preferred from this group. In these methods, the mechanical stress is by means of the respective devices applied to the cells and the engineering strain is preferably determined by optical methods.

For analysis of the engineering strain in the method according to the invention, basically all methods can be considered which are capable of applying mechanical stress on individual cells and determining the engineering strain of the cell under load application.

Appropriate devices are known from prior art. Since the property, that a statement can be made about the aggressiveness of tumor cells by analyzing their mechanical properties, was previously unknown, the invention also comprises the use of devices which are capable of applying mechanical stress as a mechanical load to a preferably individualized cell and determining the engineering strain of the cell at the time of load application, a) for diagnosis and/or prognosis of cancer by analyzing cells that are obtained from a sample of biological material from a patient, wherein the risk of tumor metastases is determined by the proportion of cells in the sample exhibiting engineering strain in the direction opposite to the direction of stressing, and possibly the risk of the presence of invasive cells by means of the mean value of the engineering strain in the direction of stressing the cells in the sample during non-linear deformation of the cell, and/or b) for determining the site of origin of a tumor of a patient with cancer by analyzing the engineering strain of tumor cells from a sample of biological material from the patient, and/or c) for screening substances as potential active substances for oncology, where the influence of a substance on the biomechanical properties of tumor cells is examined, and/or d) for the optimizing the therapy of a patient with cancer, in which the influence of different active substances on the biomechanical properties of tumor cells from the patient is examined.

Preferably, the devices are used in one of the methods according to the invention. A particularly suitable and preferred device for this is the optical stretcher. Another preferred device is an atomic force microscope. Additionally, the following devices for the uses according to the invention are preferred: a dielectrophoretic field cage, a device for the analysis of cell deformation in microfluidic flows, optical tweezers including diode laser bars and/or an ultrasound microscope.

By analyzing the mechanical properties of tumor cells, it is advantageously possible by means of suitable analysis methods to determine the aggressiveness of tumor cells without necessarily impairing their viability. It is in particular not required to mark the cells by using antibodies or similar molecules for evidencing that this is a tumor cell. This statement can be derived alone from the analysis of the engineering strain of the cell under load application.

This firstly entails the advantage that the cell can be made available after the analysis of the mechanical properties in a manner completely uncontaminated for further analysis or for cultivation. Secondly, analysis of the mechanical properties of the cells bears significant cost advantages over the use of molecular cell markers (surface markers, especially tumor markers) or marker sets. The cell markers vary greatly for each cancer, so that an individual marker set is used for all different diseases determining a specific "signature" of molecular markers. However it is not guaranteed that the selected set of molecular markers can also detect every tumor, since this signature can vary due to the diversity resulting from mutations in the tumor cells. The mechanical properties of the cells being used in a method according to the invention for prognosis or diagnosis, however, are reproducible for different forms of cancer.

The change in the engineering strain of the tumor cell being analyzed in a method according to the invention is based on the determination of changes in the cytoskeleton of the cell. Such changes can be detected using known devices with high sensitivity.

A particular advantage of the method according to the invention for prognosis and/or diagnosis of cancer is that the risk of the occurrence of tumor metastases can already be determined at a comparatively early stage, for example, from cells of the primary tumor. The risk of the occurrence of tumor metastases can there be established prior to the formation of metastases, or prior to the appearance of new tumors in distant tissues, respectively. Accordingly, the treatment of the patient can be adjusted using this information. Thereby, with knowledge of the risk of metastases, the treatment can already be aligned without the metastases being detectable or having been detected by an imaging method.

A crucial advantage of the method according to the invention for diagnosis and/or prognosis and the method for determining the site of origin of the tumor is that it is possible to make a statement as to whether there is cancer and in which tissue the primary tumor is located already from a sample of a body fluid, especially from a blood sample from a patient. In this manner it is possible to obtain much more information about a cancer type than is possible with current blood tests by using a relatively simple and inexpensive test, for example, by analyzing a blood sample. For detecting the site of origin of the tumor according to current prior art, imaging techniques are required.

By using a method for optimizing the therapy of a patient, individual selection of an appropriate active substance for each individual patient, is advantageously possible. For some tumors, for example up to 9 different chemotherapies are possible. By early and individual characterization and classification of the cancer and by screening various active substances directly on the patient's own cells, therapies can thus be selected and better customized to the patient, thereby increasing the chances of recovery and reducing costs.

Furthermore it is possible to identify new classes of active substances influencing the biomechanical properties of tumor cells such that progression of a cancer is inhibited. The screening method according to the invention is advantageous suited for this.

BRIEF DESCRIPTION OF THE DRAWINGS

By means of the following figures and embodiments, the invention is explained in more detail without limiting the invention thereto.

DESCRIPTION OF PREFERRED EMBODIMENTS

Example 1

Analysis of the Engineering Strain of Tumor Cells at Low Loads Shows the Appearance of Cells Exhibiting Engineering Strain in a Direction Opposite to the Direction of Stressing In an optical stretcher, the engineering strain of cells from malignant human breast tumors (FIG. 1*a*, black bars respectively on the left) were analyzed, which originate from tissue samples from patients with a T4-classification (distant metastases). The cells were processed and individualized using conventional methods. Subsequently, the cells were analyzed in an optical stretcher at a stress of 2 Pa. At this mechanical stress, linear deformation of the cells in the optical stretcher is to be expected. As a reference sample, cells from human breast tissue samples were analyzed from breast reductions individualized in the optical stretcher at a stress of 2 Pa (FIG. 1*a*, white bars, reference example with cells from a healthy individual). Furthermore, cells were analyzed from malignant human breast tumors from tissue samples of patients with a T1b-classification. At this stage, there are no metastases (FIG. 1*a*, black bars respectively on the right).

Figure 1:
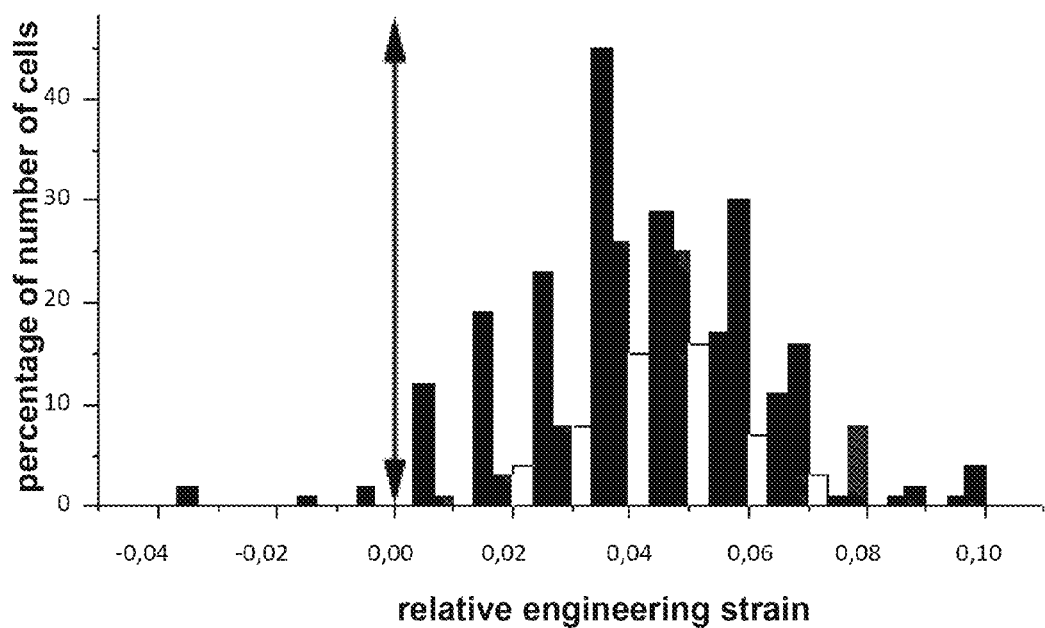
FIG. 1 shows engineering strain of cells from primary breast tumors (black bars) and healthy cells from breast reductions (white bars). The analysis was performed with the optical stretcher at a mechanical stress of 2 Pa. The black bars on the left originate from a tumor with T4-classification. The black bars on the right are from a tumor with the T 1b-classification. The double arrow shows the boundary between cells with negative and positive engineering strain. All cells were measured in HuMEC Ready medium (Invitrogen).

FIG. 1 shows the distribution of engineering strain in the samples analyzed. Only in human tissue samples from breast cancer patients with T4-classification in which there are metastases was a proportion of cells detected exhibiting engineering strain in a direction opposite to the direction of stressing ("contractile cells"). In the direction of the mechanical tension stress introduced, the diameter of these cells decreases under load application (negative engineering strain). About one in 100 cells from the tissue samples of the T4-classification exhibits this behavior.

In normal tissue, the proportion of contractile cells was below the detection limit. This also applies to cells from human tissue samples from breast cancer patients with T1b-classification.

The unexpected mechanical behavior of the tumor cells, that they exhibit engineering strain under a mechanical load being in a direction opposite to the direction of stressing, is detected only in tissue samples from patients with metastases. Contrary to non-metastatic tumor cells, these (metastatic) cells are able to leave the cell structure of the tumor tissue and pass into tissues of other origin. It is believed that certain properties of the cytoskeleton of the metastatic cells is altered in a manner that they are able to overcome the surface stress effects which normally prevent tissue cells from leaving the original cell structure (tissue). Apparently these changes in the cytoskeleton, which are present in metastatic in contrast to non-metastatic tumor cells, cause a change of the biomechanical properties to the extent, that these cells under introduced mechanical stress respond in a totally unexpected manner and show engineering strain that is not in the direction of stressing, but is directed oppositely.

Embodiment 2 was conducted as evidence for the fact that tumor cells, which under a mechanical load exhibit engineering strain in a direction opposite to the direction of stressing, exhibit biological properties than differ from other tumor cells (which in an optical stretcher exhibit engineering strain in the direction of stressing).

Example 2

Co-Culture of Tumor Cells With Normal Tissue

It was examined on the basis of a cell culture experiment whether tumor cells, which in the optical stretcher under a mechanical load of 2 Pa (range of linear deformation) exhibit contractile behavior, in the biological behavior differ from tumor cells, which under a mechanical load exhibit positive engineering strain.

For this, the cells of the following different tissue samples were examined: cells from healthy tissue of the patient's cervix were provided as normal tissue. They were in co-culture grown in droplet culture with either cells from cervical tumors of T 1b-classification (clinically apparent lesions limited to the cervix uteri) or with contractile cells from cervical tumors of T3b-classification (infestation of the lower third of the vagina and/or the pelvis wall), and T4 (distant metastases). Contractile cells were obtained from a sorting, in which the cells were deformed respectively using the optical stretcher and those cells were sorted which under mechanical stress of 2 Pa exhibited negative engineering strain. These cells were used for co-culturing with cells of normal tissue.

The cells used were individualized from the culture. For the co-culture, the same number of cells from normal tissue was respectively mixed with the respective cells from tumor tissue and grown in droplet culture in HuMEC Ready medium (Invitrogen) for 24 h.

Figure 2A:
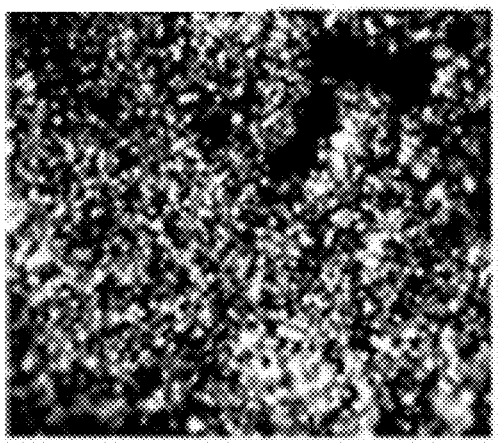
FIG. 2a, FIG. 2b, and FIG. 2c show fluorescence microscopy analysis of sorted contractile cells from tumor tissue of cervical cancer in droplet culture. Contractile cells after co-culturing with cells from normal tissue do not form an own cell structure. Co-cultures of cervical tumor cells (T1b-classification) and cervical cells a) at the start of culturing, and b) after 24 h of culturing (reference example), c) co-culture from sorted contractile cervical tumor cells (T3b- and T4-classification) with cervical cells after 24 h of culturing. Staining was conducted with red and green fluorescent dye of the CellTracker™-series from Invitrogen.

For this, the cells were stained prior to cultivation using red and green fluorescent dyes of the CellTracker™ series from Invitrogen and analyzed by fluorescence microscopy. FIG. 2*a* shows the state of the cells prior to the start of culturing.

Figure 2B:
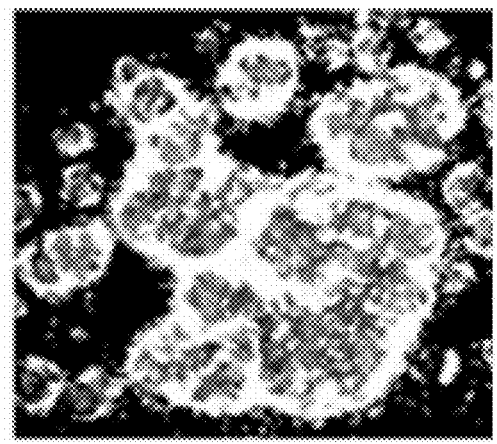
Figure 2C:
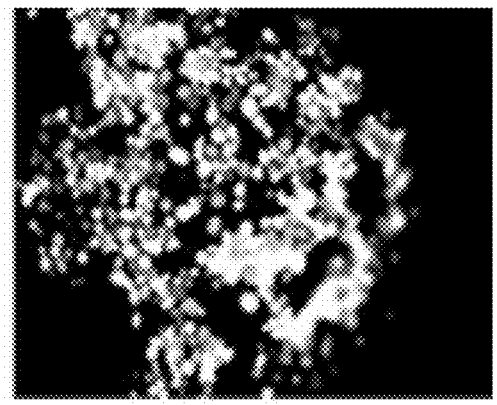

Formation of a cell structure of the tumor cells (at the center) was observed between the tumor cells from patients with T1b-classification and the cells of normal tissue (FIG. 2*b*). The tumor cells cluster together with similar cells, namely, the other tumor cells, into one cell cluster. Any mixing with cells of the normal tissue, even in the peripheral areas of the cell structure, occurs only to a small degree.

The cells from the co-culture of the sorted contractile cells from cervical tumors with T3b- and T4-classification and the normal tissue cells present a different image. After 24 hours of culturing under the same growing conditions, no formation of any cell clusters of tumor cells and cells of normal tissue was observed. The tumor cells, which under mechanical loads exhibit engineering strain behavior in a direction opposite to the direction of load application, also in the cell culture behave differently from the tumor cells, which under a mechanical load exhibit engineering strain in the direction of the stressing. The changes in the cytoskeleton are therefore associated with such a biological change of the cells, so that they lose the affinity to tissue of the same kind and are present in a homogeneous mix with other types of cells (here, the cells of the normal tissue).

Metastatic cells exhibit precisely this property of being able to leave the cell structure of the tumor and infiltrate other types of tissue. According to embodiment 1, cells whose engineering strain under a mechanical load is directed in opposite to the load application were only observed in tissue samples from patients with the formation of metastases. It can therefore be inferred by the presence of cells with these biomechanical properties in a tissue sample, that there is an increased risk of tumor metastases.

Example 3

The Deformability of Tumor Cells is Associated With Their Aggressiveness

Figure 3:
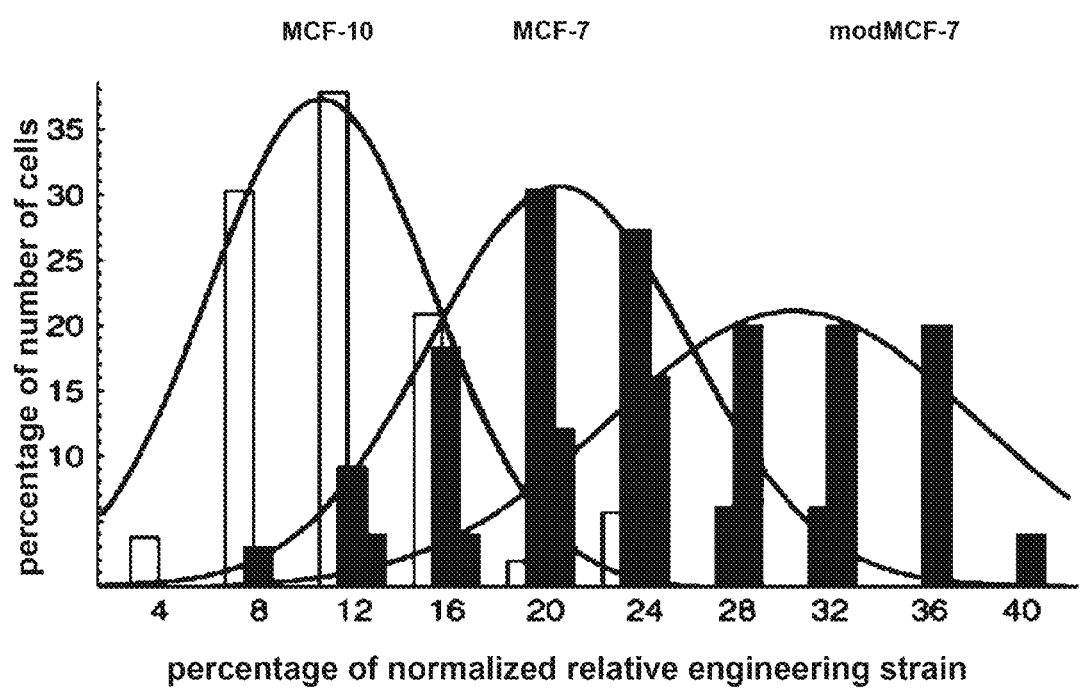
FIG. 3 shows engineering strain of cells of the cell line MCF10 (non-cancerous breast epithelial cells), MCF7 (non-metastatic tumor cells) and modMCF7 (metastatic tumor cells), determined in the optical stretcher at a mechanical stress of 5 Pa (linear deformation of the cells). Tumor cells exhibit greater engineering strain than cells from normal tissue. Further increase of engineering strain was detected in metastatic cells.

It is known from prior art that the deformability (and thus the engineering strain under a mechanical load) in tumor cells increases compared to cells from normal tissue. FIG. 3 shows this by means of a histogram demonstrating the engineering strain of the cells analyzed in the investigation following the principle of the optical stretcher.

Three cell populations from cell lines were examined: cells of the cell line MCF10 were analyzed as the normal tissue, a cell line of human non-cancerous breast epithelial cells. The cell line was derived from the breast tissue of a 36-year-old woman with mastopathy. The cell line MCF7 was used as a tumor cell line, an adenocarcinoma cell line, which was prepared from cells of a 69-year old breast cancer patient. These cells are a model for non-metastatic and non-invasive cells. If cells of the cell line MCF7 were added phorbol ester 12-O-tetradecanoylphorbol-13-acetate (TPA) (addition of 100 nmol/l TPA for 18 h in culture), then a significant increase in the invasive potential and metastasis-forming potential was observed in these cells (Johnson et al. 1999). MCF7-cells with added TPA are here referred to as "modMCF7"-cells and were used in the experiment as a model cell line for metastatic cells.

The engineering strain was determined based on the principle of the optical stretcher at a stress of 5 Pa (FIG. 3). MCF10-cells on average exhibited the least engineering strain in the direction of stressing. MCF7-cells, in comparison to MCF10-cells, on average exhibited a higher engineering strain in the direction of stressing. Furthermore, it was found that, within the sample, the engineering strain of the single cells fluctuates more, so that the standard deviation of the engineering strain, as compared to the cells in MCF10-cells, is higher for MCF7-cells. The analysis of the metastatic modMCF7-cells shows that the engineering strain on average is higher than with MCF10- as well as with MCF7-cells. The standard deviation compared to unmodified non-metastatic MCF7-cells is even higher [Guck et. al. 2005].

Figure 4:
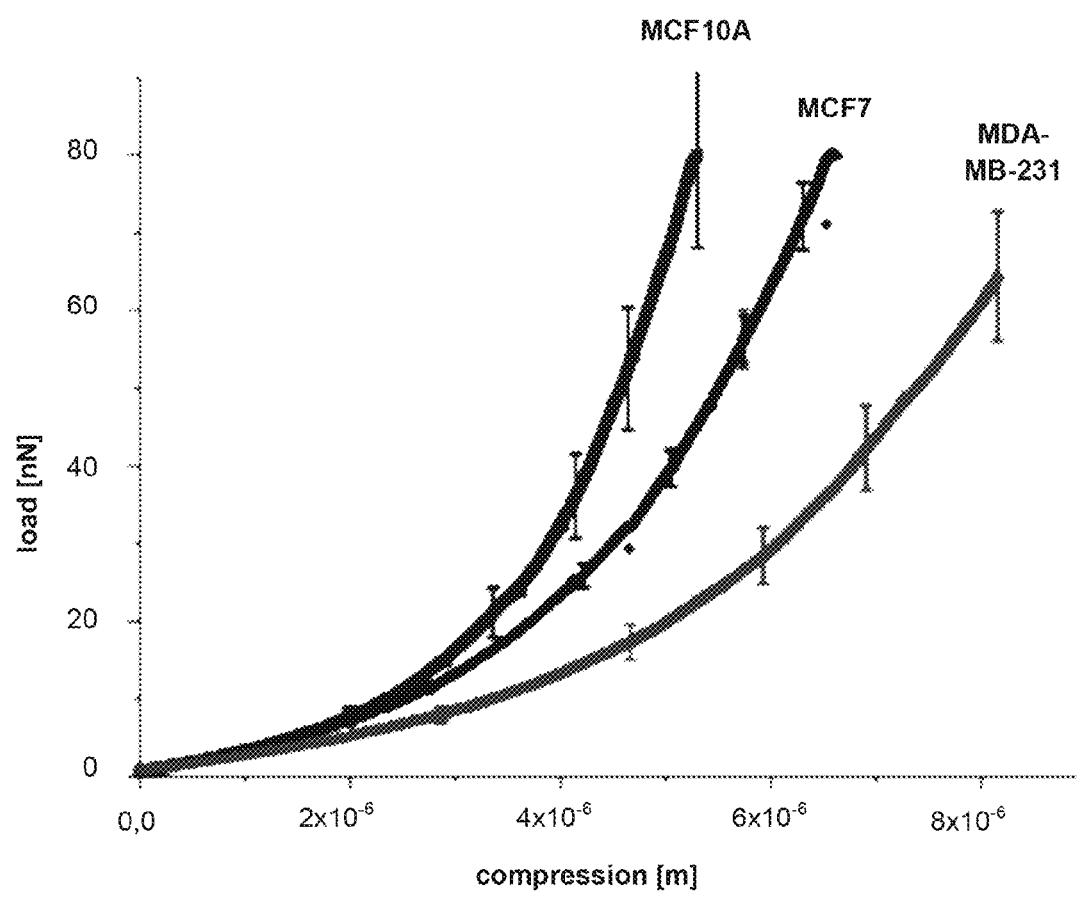
FIG. 4 shows compression of tumor cells detected by means of scanning force microscopy SFM, wherein MCF10A (non-cancerous breast epithelial cells, reference example), MCF7 (non-metastatic cancer cells), and MDA-MB-231 (metastatic cancer cells). With linear deformation, tumor cells MCF7 and MDA-MB-231 exhibit greater compression. The metastatic MDA-MB-231 exhibit the greatest compressibility.

The examination of breast tissue cell lines by means of scanning force microscopy (SFM) confirms these biomechanical properties (FIG. 4). The data was determined by constantly increasing the SFM adjustment value in the "real-time scan" mode at a rate of 1 nN/s, and recording the corresponding cantilever deflection rate at a rate of 10 Hz.

MCF10A-cells (normal tissue, ATCC-LGC Promochem, Germany) and MCF7-cells (non-metastatic, non-invasive tumor tissue, ATCC-LGC Promochem, Germany) were used. As metastatic cells, the cell line MDA-MB-231 (ATCC-LGC Promochem, Germany) was analyzed, which originates from a metastatic tumor. FIG. 4 shows that the cells during linear deformation exhibit different engineering strain properties. MCF10A-cells exhibit the lowest compression whereas the tumor cells in comparison thereto exhibit significantly higher values for compression. The metastatic MDA-MB-231-cells, when compared with non-metastatic MCF7-cells, exhibit still significantly higher compression.

Therefore, from a higher mean value of the engineering strain in the direction of stressing, a statement can be made as to whether uncontrollably proliferating cells are present.

If there is a higher mean value of the engineering strain directed in the direction of stressing in an analyzed patient sample compared with cells from normal tissues and if the cells from the patients analyzed sample simultaneously exhibit a higher proportion of cells that under stress exhibit engineering strain in a direction opposite to the direction of stressing, then there is an increased risk of the occurrence of tumor metastases.

Example 4

Simulation of the Ingrowth of Tumor Cells Into the Surrounding Tissue (Invasion)

It is assumed that the stiffening of the cells at high loads causing non-linear deformation (low engineering strain of tumor cells directed along the stressing for non-linear deformation) is responsible for tumor cells being able to grow against the surrounding normal tissue and thus can invade surrounding tissue.

Figure 5:
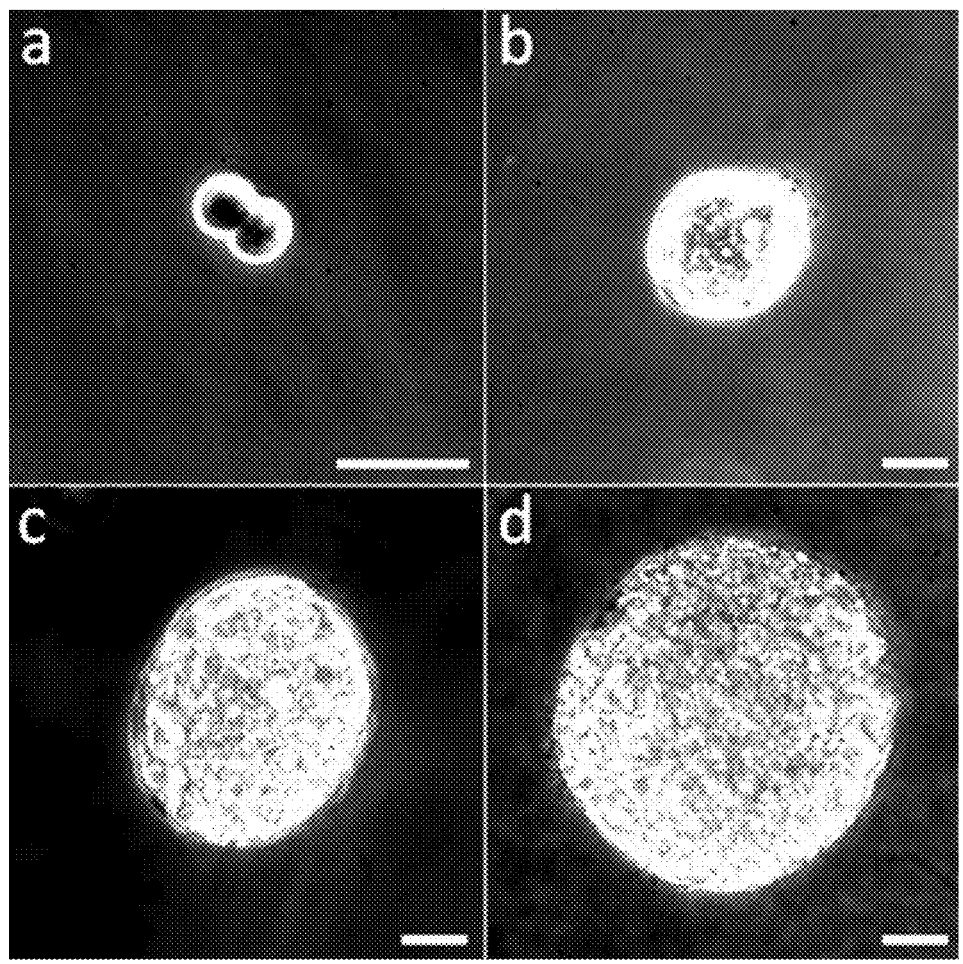
FIG. 5 shows growth of tumor cells (MCF7) as a spheroid in a hydrogel of cell culture medium containing 1% agarose with a stiffness of 1-2 kPa in culture after a) 2 days, b) 4 days, c) 14 days d) 18 days. The spheroids displace the hydrogel and grow to a stiffness of 6-10 kPa.

For detection, cells from the tumor cell line (MCF7) as well as in a further experiment, primary tumor cells from breast cancer patients were cultivated as a spheroid in a hydrogel containing 1% agarose (cell culture medium containing 1% agarose) (FIG. 5). Analysis of these cells following the principle of the optical stretcher showed that the individualized cells exhibited maximum mechanical resistance of less than 1000 Pa for linear deformation. After culturing in hydrogel, it was found that the cell structure can in the hydrogels grow against significantly higher resistances. The tumor cell spheroids in 18 days of culture grew in the hydrogel, which due to its stiffness, exerts a pressure of 6000 to 10,000 Pa (FIG. 5 $d$). The stiffness of the hydrogel was determined in the rheometer. It could thus be shown that tumor cell spheroids can withstand significantly higher mechanical stresses, than was determined by linear deformation.

Example 5

Relaxation Behavior of Tumor Cells From Primary Breast Tumors and Cells From Normal Tissue In an optical stretcher, the relaxation behavior of cells from malignant human breast tumors was analyzed and compared with the relaxation behavior of cells from a reference sample (cells of human breast tissue samples from breast reductions). The individualized cells were analyzed at 800 mW in the optical stretcher, where stress was applied for 2 seconds and the cell was observed for a further 2 seconds. With the mechanical stress introduced, linear deformation of the cells was to be expected in the optical stretcher.

Figure 6:
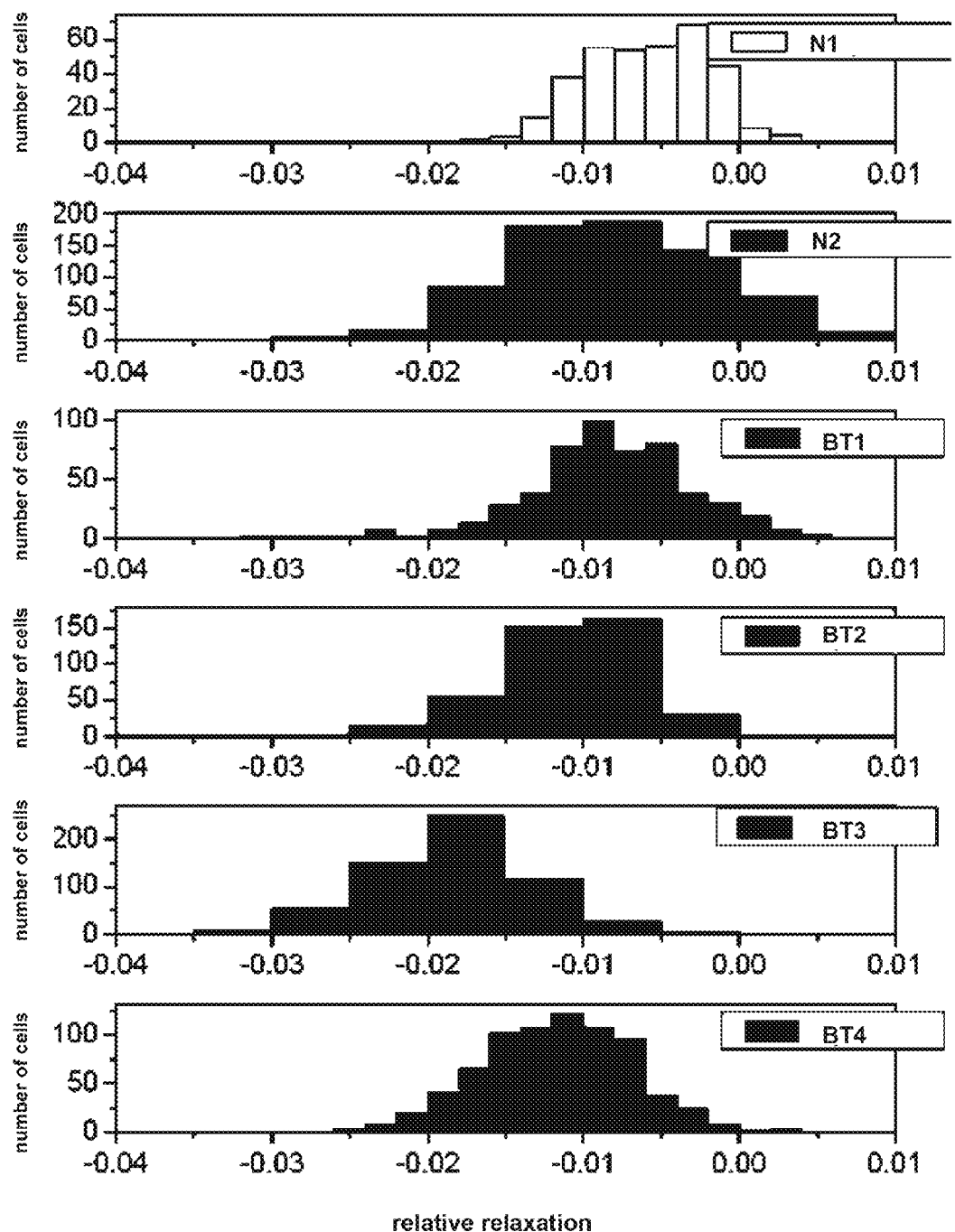
FIG. 6 shows relative relaxation of tumor cells from primary breast tumors (BT 1 to 4) and cells from normal tissue (N1, N2). The analyzed tumor cells originate from the following cancer stages: BT1 . . . stage I, BT2 . . . stage II, BT3 and BT4 . . . stage III.

Following cells were analyzed (FIG. 6):
  N1 (comparative example): primary breast epithelial cells from breast reductions (Invitrogen, HMEC cells)
  N2 (comparative example): primary breast epithelial cells from breast reductions (Promozell, HMEC cells)
  BT1: primary breast tumor stage I
  BT2: primary breast tumor stage II BT3: primary breast tumor stage III
BT4: primary breast tumor stage III
The following parameters were measured:
prior to introducing mechanical stress, the length of the cell ($L_0$)
two seconds after starting introduction of the mechanical stress (corresponds to the time $t_S$), the length of the cell ($L_S$),
two seconds after terminating introduction of the stress (corresponds to the time $t_R$), the length of the cell ($L_R$), Based on the parameters determined, the relative relaxation of the analyzed cells is determined ($R=(L_R-L_S)/L_0$). The results are exhibited in FIG. 6 where the distribution of the relative relaxation in the analyzed samples is shown.

It is seen that cells from primary breast tumors from stage II on average exhibit a lower relative relaxation, therefore exhibit stronger contraction in the original state. Furthermore, it is clear that cells of primary breast tumors from stage II do not relax only to a very small proportion (relative relaxation>0).

NON-PATENT LITERATURE CITED (Cross et al. 2007) Cross S E, Jin Y S, Rao J, Gimzewski J K. Nanomechanical analysis of cells from cancer patients. Nat Nanotechnol. 2007 December; 2(12):780-3.
(Guck et al. 2005) Guck J, Schinkinger S, Lincoln B, Wottawah F, Ebert S, Romeyke M, Lenz D, Erickson H M, Ananthakrishnan R, Mitchell D, Kas J, Ulvick S, Bilby C. Optical deformability as an inherent cell marker for testing malignant transformation and metastatic competence. Biophys J. 2005 May; 88(5):3689-98.
(Lekka at al. 1999) Lekka M, Laidler P, Gil D, Lekki J, Stachura Z, Hrynkiewicz A Z. Elasticity of normal and cancerous human bladder cells studied by scanning force microscopy. Eur Biophys J. 1999; 28(4):312-6.
(Rao & Cohen 1991) Rao K M, Cohen H J. Actin cytoskeletal network in aging and cancer. Mutat Res. 1991 March-November; 256(2-6):139-48.
(Remmerbach et al. 2009) Remmerbach T W, Wottawah F, Dietrich J, Lincoln B, Wittekind C, Guck J. Oral cancer diagnosis by mechanical phenotyping. Cancer Res. 2009 Mar. 1; 69(5)1728-32. Epub 2009 Feb. 17.
(Sanger et al. 1975) Sanger J W. Changing patterns of actin localization during cell division. Proc Natl Acad Sci USA. 1975 May; 72(5):1913-6.
(Ward et al. 1991) Ward K A, Li W I, Zimmer S, Davis T. Viscoelastic properties of transformed cells: role in tumor cell progression and metastasis formation. Biorheology. 1991; 28(3-4):301-13.

What is claimed is:

1. A method for diagnosis and/or prognosis of cancers comprising the analysis of the engineering strain of cells subjected to a mechanical load, said cells obtained from a sample of tissue from a patient, the method comprising the steps of:
a) applying a mechanical load to each cell such that linear deformation of said cell is to be expected, wherein said mechanical load is applied to said cell by an optical stretcher/tweezers;
b) determining by optical methods said engineering strain on said cell in the direction of load application at the time of applying said mechanical load,
c) repeating steps a) and b) for a plurality of cells and determining a distribution of the determined engineering strain for all analyzed cells,
d) determining the proportion of cells in said sample, which under a mechanical load exhibit engineering strain in a direction opposite to the direction of stressing,
e) comparing the proportion of cells of step d) with reference data obtained by treating cells of the same type of tissue of one or more healthy individuals or of healthy tissue from the same patient according to steps a) to d), and
f) determining that the patient is at risk of tumor metastases when a proportion of cells, that under a mechanical load exhibit engineering strain in a direction opposite to the direction of stressing, is higher in said sample than said reference data.

2. The method according to claim 1, further comprising:
determining the mean value of said engineering strain of said analyzed cells in said sample, which under a mechanical load exhibit engineering strain in a direction of stressing;
comparing said mean value of said engineering strain of said analyzed cells with a reference mean value of the engineering strain in a direction of stressing of said reference data, and
determining that a higher risk of the presence of uncontrollably proliferating cells exists when said mean value of said engineering strain of said analyzed cells is higher than said reference mean value.

3. The method according to claim 1, further comprising:
g) applying the mechanical load as a deforming mechanical stress to at least one cell of the said sample such that non-linear deformation of said cell is to be expected;
h) determining the engineering strain on said cell at the time of applying said deforming mechanical stress;
i) optionally carrying out the steps of applying the mechanical load as a deforming mechanical stress and determining the engineering strain on said cell at the time of applying said deforming mechanical stress on several cells of said sample and determining the mean value of said engineering strain of said several analyzed cells of said sample;
j) comparing the determined engineering strain of step h) or the mean value of the engineering strain of step i) with reference data obtained by treating cells of the same type of tissue of one or more healthy individuals or of healthy tissue from the same patient according to steps g) to i), and
k) determining that a higher risk of the presence of invasive cells exists when the determined engineering strain of step h) or the mean value of the engineering strain of step i) is higher than the reference data.

4. The method according to claim 1, wherein said cells are isolated from tumor tissue of the patient.

5. The method according to claim 1, further comprising:
A) determining the length of each respective cell from said sample without applying any mechanical stress,
B) subsequently applying the mechanical load as a mechanical stress, at which linear deformation of said cell is to be expected, to said cell at a time $i_S$ and determining said length of said cell under said mechanical stress,
C) subsequently, without applying said mechanical stress, determining said engineering strain of said cell after its relaxation at a time $t_R$,
D) determining the relative relaxation by forming the difference in said engineering strain of said cell under said mechanical stress at the time $i_S$ and said engineering strain of said cell after relaxation of said cell at the time $t_R$, E) repeating steps A) to D) for determining the relative relaxation of a plurality of cells and determining a distribution of the determined relative relaxation for all analyzed cells, F) comparing said distribution of the relative relaxation of said cells in said sample with reference data obtained by treating cells of the same type of tissue of one or more healthy individuals or of healthy tissue from the same patient according to steps A) to E), and G) determining that a high risk of the presence of uncontrollably proliferating cells exists when a relative relaxation in said sample on average is lower than said reference data and/or a number of cells in said sample having a relative relaxation of more than 0 is smaller than a number of cells of said reference data.

6. The method according to claim 1, wherein, when tumor cells are found in said sample, for diagnosis of the tissue of origin of said tumor cells, the engineering strain of said tumor cells under a mechanical load is analyzed, comprising the steps of:

A) applying deforming mechanical stress as a mechanical load to a plurality of said tumor cells such that linear or non-linear deformation of said tumor cells is to be expected, respectively, and determining said engineering strain on said tumor cells at the time of applying said mechanical load, B) determining a distribution of the determined engineering strain for all analyzed tumor cells that show an engineering strain in the direction of the applied deforming mechanical stress, C) determining the mean value of said engineering strain in the direction of stressing said tumor cells from said determined distribution, D) comparing said mean value with different sets of reference data, wherein each set of reference data is obtained by treating cells of a particular human tissue of one or more healthy individuals according to steps A) to C), and E) selecting the tissue of said reference data set, for which the value of the difference of said mean values of engineering strain between said sample and said reference data set is least, as the tissue of origin of said tumor.

7. The method according to claim 1, wherein said cells are individualized before analysis such that each cell can be analyzed individually.

* * * * *